(12) United States Patent
Lloyd et al.

(10) Patent No.: US 8,877,173 B2
(45) Date of Patent: Nov. 4, 2014

(54) WEATHER RESISTANT GRANULAR SLUG, SNAIL AND INSECT BAIT

(75) Inventors: Jeffrey D. Lloyd, Knoxville, TN (US); Janet Kintz-Early, Knoxville, TN (US)

(73) Assignee: Nisus Corporation, Rockford, TN (US)

( * ) Notice: Subject to any disclaimer, the term of this patent is extended or adjusted under 35 U.S.C. 154(b) by 868 days.

(21) Appl. No.: 12/572,309

(22) Filed: Oct. 2, 2009

(65) Prior Publication Data

US 2010/0021418 A1    Jan. 28, 2010

Related U.S. Application Data

(63) Continuation-in-part of application No. 10/928,510, filed on Aug. 27, 2004, now abandoned.

(51) Int. Cl.
*A01N 25/00* (2006.01)
*A01N 59/14* (2006.01)

(52) U.S. Cl.
CPC ............. *A01N 25/008* (2013.01); *A01N 59/14* (2013.01)
USPC ........................................................ 424/84

(58) Field of Classification Search
CPC .............................. A01N 25/008; A01N 59/14
See application file for complete search history.

(56) References Cited

U.S. PATENT DOCUMENTS

| | | |
|---|---|---|
| 4,996,053 A | 2/1991 | Hatcher |
| 6,007,832 A | 12/1999 | Stapleton |
| 6,645,949 B1 | 11/2003 | Nigg et al. |
| 7,045,138 B2 | 5/2006 | Kennedy et al. |
| 7,223,415 B1 | 5/2007 | Malone et al. |

FOREIGN PATENT DOCUMENTS

| | | |
|---|---|---|
| AU | 2003203735 | 11/2003 |
| DE | 10132532 | 2/2003 |
| EP | 0248991 | 12/1987 |
| JP | 62-195301 | 8/1987 |
| WO | WO 92/22205 | 12/1992 |
| WO | WO 95/35029 | 12/1995 |
| WO | WO 00/11948 | 3/2000 |
| WO | WO 00/15033 | 3/2000 |
| WO | WO 01/17348 | 3/2001 |
| WO | WO 01/87559 | 11/2001 |
| WO | WO 02/06417 | 1/2002 |

OTHER PUBLICATIONS

Milanez, J.M.; Chiraradia, L.A., Efficiency of baits with boric acid to control Sarasinula linguaaformis (Semper 1885) 9Mollusea, Veroniccidae), Pesquisa Agropecuaria Gaucha, vol. 5, No. 2 pp. 351-355 (1990) (1 page abstract).

*Primary Examiner* — James D Anderson
(74) *Attorney, Agent, or Firm* — Luedeka Neely Group, P.C.

(57) ABSTRACT

The present disclosure is directed to a physical and chemical formulation designed to be attractive to, and eaten by, terrestrial mollusks, specifically slugs and snails. Optionally, the formulation is also attractive to and toxic to insects. Upon being eaten and after a set delay, the invention is designed to kill such pests and in so doing remove them from the premises or environment treated.

22 Claims, 4 Drawing Sheets

WEATHER RESISTANT GRANULAR SLUG, SNAIL AND INSECT BAIT

CROSS-REFERENCE TO RELATED APPLICATIONS

This application is a continuation-in-part of co-pending application Ser. No. 10/928,510, filed Aug. 27, 2004, entitled "Weather Resistant Granular Slug, Snail and Insect Bait."

FIELD

The present disclosure relates in general to pest control formulations, and in particular, to a bait formulation suitable for use in controlling terrestrial mollusks.

BACKGROUND

Terrestrial mollusks, such as slugs and snails, are herbivores capable of extensively damaging plants, including flowers, vegetables, and some trees and shrubs. Not only can terrestrial mollusks be quite damaging, existing baits designed to exterminate them often have significant limitations. For example, the baits do not always perform well in the natural environments of mollusks, which is often permanently moist or frequently wet. Existing baits also sometimes lose their physical integrity under such circumstances or lose their efficacy upon prolonged exposure to moisture, sunlight, or both.

In addition, many slugs and snails live in environments where damaging insects are also present. Although control of these insects is desirable, it is often preferable to exterminate the insects without use of a contact pesticide that will indiscriminately kill non-targeted insects, or that will function only for a short period of time after application. Desirably, a method of controlling slugs and snails could also be used to control insect pest populations.

A further challenge is that some slug and snail baits presently in use are not properly formulated for consumption by mollusks, either because they do not have a proper attractant in appropriate concentration, or because they are not physically formed in a manner that promotes consumption by mollusks, and especially not consumption by both mollusks and insects.

Therefore, a need exists for an improved formulation for control of terrestrial mollusks, especially one that can also be used to control targeted insect pest populations. Any such formulation should desirably also be well suited toward use in moist environments without excessive loss of physical integrity or efficacy as a pest control material. Finally, the composition should be formulated such that it is highly attractive to both mollusks and insects.

SUMMARY

The present invention is directed to a physical and chemical formulation designed to be attractive to, and eaten by, terrestrial mollusks, specifically slugs and snails. Optionally it is also attractive to and consumed by insect pests. Upon being eaten, and after a set delay, the invention is designed to kill such pests.

The physical and chemical formulation of the pest control composition of the invention includes a bait with broad spectrum performance against insect pests, many general arthropod pests, and also snails and slugs. The formulation provides excellent weathering capabilities and lasting protection with repeated applications. The chemical and physical formulation of the invention shows, in certain implementations, resistance to ultraviolet light, resistance to water, and resistance to oxidation and hydrolysis, while being highly effective against slugs and snails.

In a first aspect, the invention is directed to a pest control composition active against arthropods (including insects) and terrestrial mollusks, the composition comprising a borate-containing agent toxic to both insects and mollusks, but substantially non-repellant to both insects and mollusks. The composition also typically includes a carrier matrix. The carrier matrix serves to bind the borate-containing agent together, with other materials included in the composition, such as carbohydrates (including sugars), proteins, or fats (or whole food materials containing these components—e.g. cereals, dried vegetables or fruits or nuts) used as attractants.

The borate active ingredient comprises, for example, boric acid. The boric acid optionally comprises from 0.1 to 10 percent of the pest control composition based upon total dry weight of the composition. The amount of boric acid can be less than 20 percent in some embodiments, and less than 10 percent in certain embodiments, based upon total dry weight of the pest control composition. In general the borate active ingredient, such as boric acid, comprises at least 1 percent of the pest control composition, based upon total dry weight of the pest control composition.

The active ingredient of the pest control formulation is typically blended with a carrier matrix containing an organic material, such as corncobs or nut husks or vegetable derived meal. In some embodiments the carrier matrix comprises an organic material having food value to terrestrial mollusks. Suitable organic material having food value to terrestrial mollusks includes oils, sugars, fruit extracts, vegetable extracts, proteins and combinations thereof. Whole food materials containing these components—e.g. cereals, dried vegetables or fruits or nuts—can also be used as attractants.

A specific acceptable example formulation contains at least about 50 percent of an organic carrier and more desirably at least about 60 to 90 percent organic carrier; at least about 5 percent oil and more desirably from about 10 to 20 percent oil; at least about 5 percent carbohydrate, such as a sugar, often about 5 to 20 percent sugar; and at least about 2 percent but desirably less than about 15 percent of a borate-containing composition. The borate-containing composition is preferably boric acid or borax.

A specific example of a formulation that can be used within the scope of the invention contains approximately 70 percent corncob matter; approximately 15 percent corn oil; approximately 10 percent sugar; and approximately 5 percent boric acid, wherein all percentages are based upon dry weight of the pest control composition.

The unique formulation made in accordance with the invention is generally durable under environmental conditions in which terrestrial mollusks thrive, including moist environments. Thus, the pest control composition desirably retains its physical integrity after being exposed to the weather (precipitation, UV light, heat, air oxidation and hydrolysis and leaching) for 1 week or more. Similarly, the pest control composition substantially retains its efficacy after being exposed to the weather (precipitation, UV light, air oxidation and hydrolysis and leaching) for an extended period of time, such as one month under many circumstances. Typically the pest control composition remains effective under normal outdoor weather conditions in temperate climates for a period of one month or more. Such climates include, for example, one in which approximately four inches of accumulated rain fall during that period and the temperature remains between about 40 and 100 degrees Fahrenheit.

In a further aspect, the present disclosure also provides a pest control composition which is durable under wet or moist environmental conditions in which terrestrial mollusks live. In one embodiment, the pest control composition includes from about 1 to about 15 percent of a borate-containing active ingredient; from about 52 to about 75 percent of a cellulosic carrier matrix material selected from the group consisting of ground corn cobs, straw, wood particles, rice hulls, and combinations thereof; from about 10 to about 20 percent of an oil-based attractant; from about 1 to about 8 percent of a protein-based attractant; from about 5 to about 15 percent of a sugar-based attractant; and from about 5 to about 15 percent of a flour-based attractant, wherein all weight percentages are based upon dry weight of the pest control composition.

The present disclosure also provides a method of controlling terrestrial mollusks in a wet or moist environment. In one embodiment, the method includes a first step of providing a pest control composition which is durable under wet or moist environmental conditions in which terrestrial mollusks live and which includes from about 1 to about 15 percent of a borate-containing active ingredient; from about 52 to about 75 percent of a cellulosic carrier matrix material selected from the group consisting of ground corn cobs, straw, wood particles, rice hulls, and combinations thereof; from about 10 to about 20 percent of an oil-based attractant; from about 1 to about 8 percent of a protein-based attractant; from about 5 to about 15 percent of a sugar-based attractant; and from about 5 to about 15 percent of a flour-based attractant, wherein all weight percentages are based upon dry weight of the pest control composition. The method further includes applying the pest control composition to a wet or moist environment which is infested with terrestrial mollusks; and attracting terrestrial mollusks with the pest control composition so that the terrestrial mollusks ingest a lethal amount of the pest control composition.

In certain embodiments, the borate-containing active ingredient is preferably selected from the group consisting of boric acid, boric oxide, sodium tetraborate, disodium octaborate, sodium pentaborate, and combinations thereof. More preferably, the borate-containing active ingredient includes boric acid.

In other embodiments, the oil-based attractant is selected from the group consisting of corn oil, peanut oil, soybean oil, palm oil, sunflower oil, rapeseed oil, and combinations thereof. More preferably, the oil-based attractant includes corn oil.

In some embodiments, the sugar-based attractant is preferably selected from the group consisting of sucrose, dextrose, glucose, fructose, honey, corn syrup, maple syrup, and combinations thereof. More preferably, the sugar-based attractant includes sucrose.

The flour-based attractant preferably includes wheat flour or corn flour.

In certain embodiments, the protein-based attractant is preferably selected from the group consisting of soy-derived protein, egg-derived protein, myco-derived protein, bacteria-derived protein, fish-derived protein, insect-derived protein, bovine-derived protein, porcine-derived protein, and combinations thereof. More preferably, the protein-based attractant comprises egg-derived protein.

In one embodiment according to the present disclosure, the pest control composition most preferably includes about 5 percent of a borate-containing active ingredient; about 57 percent of ground corn cobs; about 15 percent of an oil-based attractant; about 3 percent of a protein-based attractant; about 10 percent of a sugar-based attractant; and about 10 percent of a flour-based attractant.

In certain embodiments, the flour-based attractant preferably comprises particles having a particle size distribution such that at least about 80 weight percent of the flour-attractant particles pass through a number 14 U.S. standard sieve mesh screen and no more than about 20 weight percent of the flour-attractant particles pass through a number 40 U.S. standard sieve mesh screen.

In still another aspect, the present disclosure also a pest control composition which is durable under wet or moist environmental conditions in which terrestrial mollusks live. In one embodiment, the pest control composition includes from about 1 to about 15 percent of a borate-containing active ingredient; from about 1 to about 10 percent of an oil-based attractant; from about 1 to about 8 percent of a protein-based attractant; from about 5 to about 15 percent of a sugar-based attractant; and from about 72 to about 82 percent of a flour-based attractant, wherein all weight percentages are based upon dry weight of the pest control composition. This pest control formulation is particularly suitable for forming pellets.

The present disclosure also provides a method of controlling terrestrial mollusks in a wet or moist environment. In one embodiment, the method includes a first step of providing a pest control composition which is durable under wet or moist environmental conditions in which terrestrial mollusks live and which includes from about 1 to about 15 percent of a borate-containing active ingredient; from about 1 to about 10 percent of an oil-based attractant; from about 1 to about 8 percent of a protein-based attractant; from about 5 to about 15 percent of a sugar-based attractant; and from about 72 to about 82 percent of a flour-based attractant, wherein all weight percentages are based upon dry weight of the pest control composition. The method further includes applying the pest control composition to a wet or moist environment which is infested with terrestrial mollusks; and attracting terrestrial mollusks with the pest control composition so that the terrestrial mollusks ingest a lethal amount of the pest control composition.

In certain embodiments, the borate-containing active ingredient is preferably selected from the group consisting of boric acid, boric oxide, sodium tetraborate, disodium octaborate, sodium pentaborate, and combinations thereof. More preferably, the borate-containing active ingredient includes boric acid.

In other embodiments, the oil-based attractant is selected from the group consisting of corn oil, peanut oil, soybean oil, palm oil, sunflower oil, rapeseed oil, and combinations thereof. More preferably, the oil-based attractant includes corn oil.

In some embodiments, the sugar-based attractant is preferably selected from the group consisting of sucrose, dextrose, glucose, fructose, honey, corn syrup, maple syrup, and combinations thereof. More preferably, the sugar-based attractant includes sucrose.

The flour-based attractant preferably comprises wheat flour or corn flour.

In certain embodiments, the protein-based attractant is preferably selected from the group consisting of soy-derived protein, egg-derived protein, myco-derived protein, bacteria-derived protein, fish-derived protein, insect-derived protein, bovine-derived protein, porcine-derived protein, and combinations thereof. More preferably, the protein-based attractant comprises egg-derived protein.

In one embodiment according to the present disclosure, the pest control composition most preferably includes about 5 percent of a borate-containing active ingredient; about 5 percent of an oil-based attractant; about 3 percent of a protein-based attractant; about 10 percent of a sugar-based attractant; and about 77 percent of a flour-based attractant.

BRIEF DESCRIPTION OF THE DRAWINGS

The invention is also described in accordance with the following figures.

DETAILED DESCRIPTION

Figure 1:
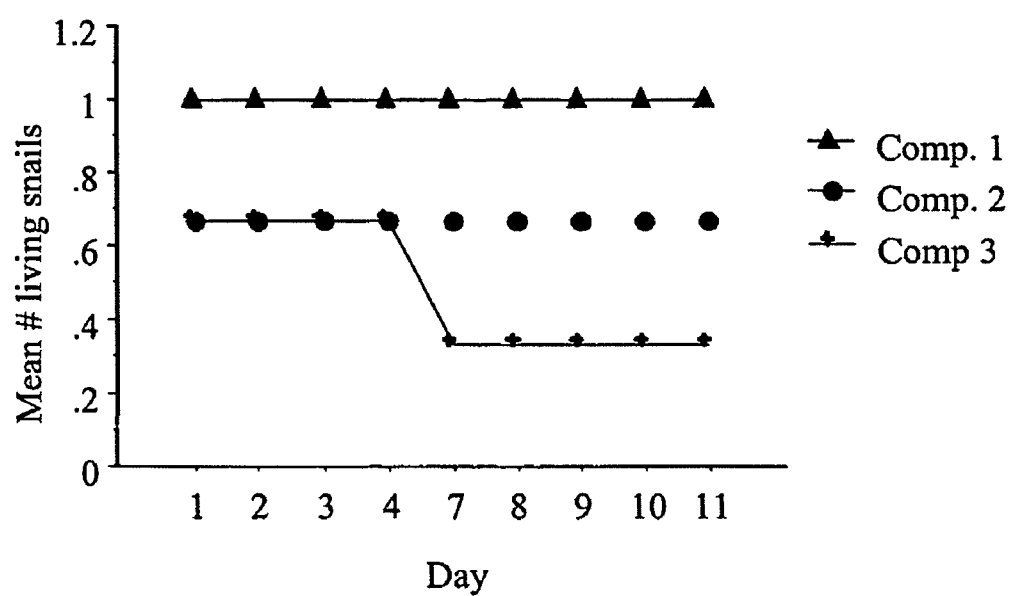
FIG. 1 is a chart showing the efficacy of compositions made in accordance with the invention at exterminating terrestrial mollusks.

The present invention is directed to a physical and chemical formulation designed to be attractive to, and eaten by, terrestrial mollusks, specifically slugs and snails. Optionally, the formulation is also attractive to and toxic to insects. Upon being eaten and after a set delay, the invention is designed to kill such pests and in doing so remove them from the premises or environment treated. The pest control formulation of the present invention typically includes a granular bait with broad spectrum performance against snails and slugs, as well as general insect pests. The formulation also provides excellent weathering capabilities, making it well suited to use in moist environments and locations where it will be exposed to the environment. Such weathering properties are very desirable, if not essential, because the habitat in which snails and slugs are most commonly located are relatively wet and have high humidity.

In a first aspect, the invention is directed to a pest control composition comprising a borate-containing agent toxic to both insects and mollusks, but substantially non-repellant to both insects and mollusks. The composition also includes a carrier matrix. The carrier matrix serves to bind the borate-containing agent together, with other materials included in the composition, such as carbohydrates, proteins, or fats, used as attractants.

The unique formulation made in accordance with the invention is generally durable under environmental conditions in which terrestrial mollusks thrive, including moist environments. Thus, the pest control composition desirably retains its physical integrity after being exposed to the weather (precipitation, UV light, heat, air oxidation, hydrolysis and leaching) for at least 1 week. Similarly, the pest control composition substantially retains its efficacy after being exposed to the weather (precipitation, UV light, air oxidation, hydrolysis and leaching) for 1 month under many circumstances. Although the composition can be administered in various forms, it is advantageous to be administered to pests in a granular form of varying particle sizes to allow easy ingestion by a range of slug and snail and insect sizes and species.

Additional aspects of the invention will now be described in greater detail below:

Active Ingredient

The pest control formulation of the present invention typically includes a borate-containing active ingredient. In general, the borate-containing active ingredient may be selected from the group consisting of boric acid, boric oxide, sodium tetraborate, disodium octaborate, sodium pentaborate, and combinations thereof. More preferably, the borate-containing active ingredient includes boric acid. In general the borate active ingredient, such as boric acid, comprises at least 1 percent of the pest control composition, based upon total dry weight of the pest control composition. In some implementations, the boric acid optionally comprises from 0.1 to 10 percent of the pest control composition based upon total dry weight of the pest control composition. The amount of boric acid can be less than 20 percent in some embodiments, and less than 10 percent in certain embodiments, based upon total dry weight of the pest control composition. In certain embodiments, the pest control composition includes from about 1 to about 15 percent of a borate-containing active ingredient.

Matrix Material

The borate-containing active ingredient of the pest control formulation is typically, but not always, blended with a carrier matrix containing an organic material, such as corncobs, or plant derived materials such as shells, hulls, husks or meal. For instance, the pest control formulation may include from about 52 to about 75 percent of a cellulosic carrier matrix material selected from the group consisting of ground corn cobs, straw, wood particles, rice hulls, and combinations thereof. Ground corn cobs are particularly preferred carrier matrix material. Other organics, both inert and of food value, such as cereals, rice, dried fruit or vegetables or nuts or extracts, can be used. In some embodiments, the carrier matrix comprises an organic material having food value to terrestrial mollusks. Suitable organic material, having food value to terrestrial mollusks, includes oils, sugars, fruit extracts, vegetable extracts, proteins and combinations thereof (or whole food materials containing these components—e.g. cereals, dried vegetables or fruits or nuts or processed waste food materials).

Attractants

The pest control composition also preferably includes one or more food ingredients which act as an attractant for the terrestrial mollusks. For instance, the pest control composition may include one or more sugar-based attractants, one or more oil-based attractants one, one or more protein-based attractants and/or more flour-based attractants.

Preferred sugar-based attractants may be selected from the group consisting of sucrose, dextrose, glucose, fructose, honey, corn syrup, maple syrup, and combinations thereof. A particularly preferred sugar-based attractant is sucrose.

Preferred oil- or fat-based attractants may be selected from the group consisting of corn oil, peanut oil, soybean oil, palm oil, sunflower oil, rapeseed oil, and combinations thereof. Corn oil is a particularly preferred oil-based attractant.

Preferred protein-based attractants may be selected from the group consisting of soy-derived protein, egg-derived protein, myco-derived protein, bacteria-derived protein, fish-derived protein, insect-derived protein, bovine-derived protein, porcine-derived protein, and combinations thereof. More preferably, the protein-based attractant comprises egg-derived protein.

Preferred flour-based attractants include wheat flour and corn flour. In some embodiments, the flour-based attractant may be used in substitution for all or a portion of the carrier matrix material discussed above.

For example, in an embodiment using a relatively large amount of carrier matrix and a relevantly small amount of flour-based attractant, the pest control composition may include from about 1 to about 15 percent of a borate-containing active ingredient; from about 52 to about 75 percent of a cellulosic carrier matrix material; from about 10 to about 20 percent of an oil-based attractant; from about 1 to about 8 percent of a protein-based attractant; from about 5 to about 15 percent of a sugar-based attractant; and from about 5 to about 15 percent of a flour-based attractant, wherein all weight percentages are based upon dry weight of the pest control composition. More preferably, the pest control composition may be composed of about 5 percent of a borate-containing active ingredient; about 57 percent of ground corn cobs; about 15 percent of an oil-based attractant; about 3 percent of a protein-based attractant; about 10 percent of a sugar-based attractant; and about 10 percent of a flour-based attractant.

In another embodiment, however, the carrier matrix material may be omitted while the amount of flour-based attractant is substantially increased. The pest control composition may include from about 1 to about 15 percent of a borate-containing active ingredient; from about 1 to about 10 percent of an oil-based attractant; from about 1 to about 8 percent of a protein-based attractant; from about 5 to about 15 percent of a sugar-based attractant; and from about 72 to about 82 percent of a flour-based attractant, wherein all weight percentages are based upon dry weight of the pest control composition. More preferably, the pest control composition may be composed of about 5 percent of a borate-containing active ingredient; about 5 percent of an oil-based attractant; about 3 percent of a protein-based attractant; about 10 percent of a sugar-based attractant; and about 77 percent of a flour-based attractant. It has been found that this pest control formulation is particularly suitable for forming pellets.

EXAMPLE FORMULATIONS

Various formulations may be made in accordance with the invention. A specific acceptable formulation contains at least about 50 percent of an organic carrier and more specifically at least about 60 to 90 percent carrier; at least about 5 percent oil and more desirably from about 10 to 20 percent oil; at least about 5 percent carbohydrate, such as a sugar, often about 5 to 20 percent sugar; and at least about 2 percent but desirably less than about 15 percent of a borate-containing composition. The borate-containing composition is preferably boric acid or borax.

A specific example of a material that can be used for the invention contains approximately 70 percent corncob matter; approximately 15 percent corn oil; approximately 10 percent sugar; and approximately 5 percent boric acid, wherein all percentages are based upon dry weight of the pest control composition.

During production the components are blended together in an essentially dry process that intimately combines the components and produces specific sized granules that are able to perform for extended time periods and rainfall in exterior situations. In a specific implementation of the invention, powdered sugar is mixed with boric acid and ground corncob. Corn oil is then added and mixing continues for approximately 20 to 25 minutes to produce a granular composition well suited to slug and snail control. In the alternative, a wet process with binder (e.g. agar, gelatin, wheat flour, corn meal etc. with water) can be used to produce molded solid forms that break off into granules.

In some embodiments, two attractants or food sources are used with the bait to give it a broader appeal to various target pests. The use of two attractants (such as corn oil and confectioner's sugar) gives a synergistic performance. Tested separately these components are known to not be good attractants for all target pests. In addition to these two attractants in the invention, the further addition of a protein source (e.g. yeast extract, soy, albumin etc.) and an additional carbohydrate source (e.g. wheat, corn, oat, rice or potato flour, or malt extract, dried fruit, nut or vegetable etc.) is not excluded from the invention.

A preferred granular size is within the ranges of #14 Mesh to #100 Mesh. The particle sizes being distributed in this range have been found to provide ample foraging opportunities for many different pest species and size ranges such as cockroaches, silverfish, crickets, snails, slugs and numerous ant species including fire, argentine, odorous house, carpenter, and pavement ants). If only the molluscicide part of the formulation (not insecticide part) is to be used, a larger pellet rather than a granule is preferred (e.g. 1-5 mm×3-10 mm) for improved longevity.

Furthermore, the major advantages of using borates as pesticides (broad spectrum, low relative cost, low acute mammalian toxicity and low environmental impact), are retained. This therefore, represents a major advantage to existing technology in the control of general insect, arthropod and land mollusk pests. This discovery can provide immediate benefit to homeowners and pest management professionals who want an effective long term, broad spectrum, flexible control strategy that incorporates the benefits of a borate molluscicide and insecticide.

Efficacy

The following test was conducted to confirm the efficacy of formulations made in accordance with the invention on exterminating snails and slugs. Snails and slugs were collected from outdoors in Knox County, Tenn. Snails, slugs and water soaked cotton pads were placed in a disposable plastic container at the start of the study. A total of three or four snails and slugs, consisting of zero to one snail and two to three slugs, were placed in each of nine 739 ml disposable plastic containers. An 8 cm disposable petri dish, which held wet cotton and 1.6 gm granular bait treatment, was also placed in each container. Granular bait treatments consisted of a carrier material and attractant without a molluscicide, a carrier material and attractant with boric acid active ingredient, plus a carrier material, attractant, and iron phosphate (an industry standard molluscicide). When the composition was formulated with iron phosphate or without any pesticide, the percentage of inert ingredients was increased accordingly.

Figure 2:
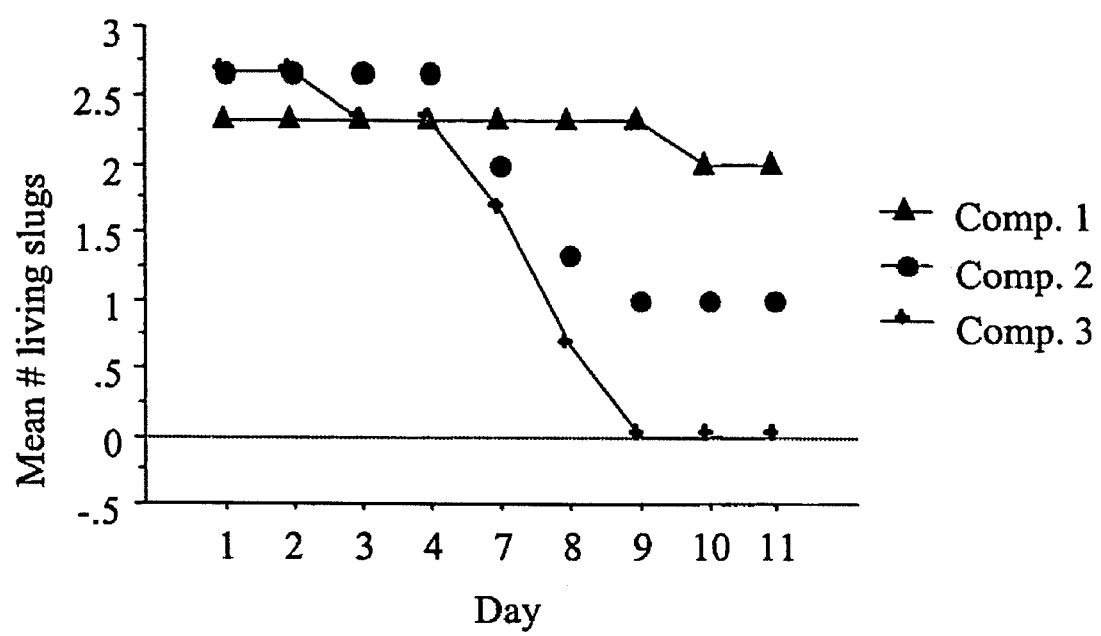
FIG. 2 is a second chart showing the efficacy of compositions made in accordance with the invention at exterminating terrestrial mollusks.
Figure 3:
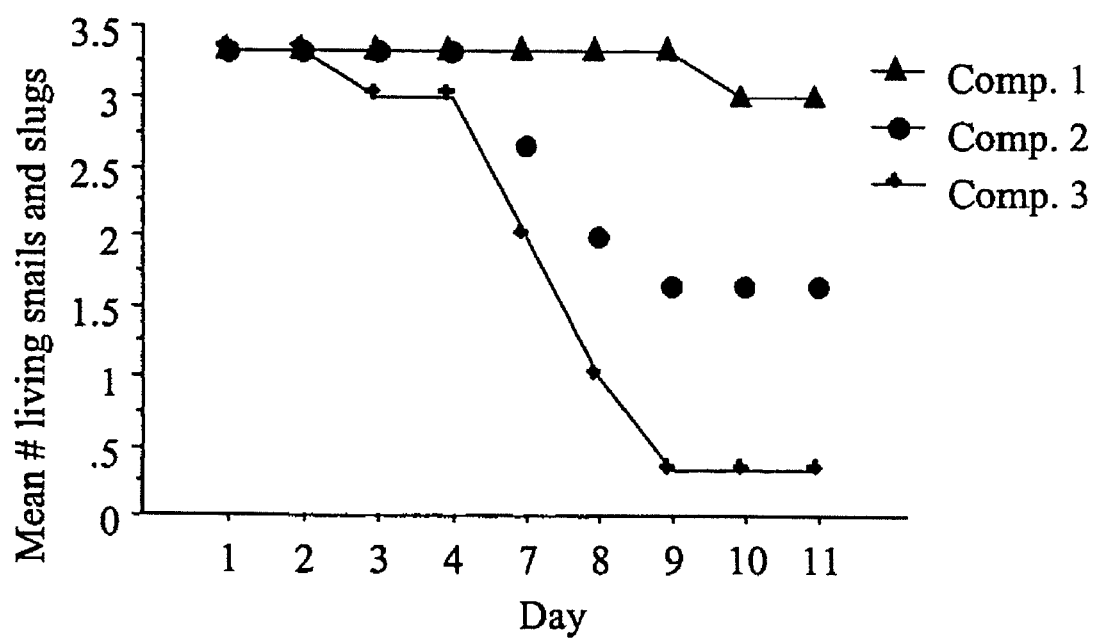
FIG. 3 is a third chart showing the efficacy of compositions made in accordance with the invention at exterminating terrestrial mollusks.

The results of this study are shown below in FIGS. 1, 2, and 3. FIG. 1 shows the mean number of living snails observed after eleven days of exposure to 1.6 grams of granular bait treatments. The first composition contained a control with only food attractants, while the second composition contained 1 percent $FePO_4$, and the third composition contained five percent $H_3BO_3$. 2 shows the mean number of living slugs observed after eleven days of exposure to 1.6 grams of granular bait treatments. The first composition contained a control with only food attractants, while the second composition contained 1 percent $FePO_4$, and the third composition contained five percent $H_3BO_3$. FIG. 3 shows the mean number of living snails and slugs observed after eleven days of exposure to 1.6 grams of granular bait treatments. The first formulation contained a control with only food attractants, while the second composition contained 1 percent $FePO_4$, and the third composition contained five percent $H_3BO_3$.

The results show that boric acid was more effective than iron phosphate and the control at killing snails and slugs. On day 11, the mean number of living slugs and snails were 0 and 0.3, respectively. By day 7, the control bait and the iron phosphate bait had gone moldy while the boric acid bait had not. Published studies have also indicated that snail and slug baits go moldy in a short period of time (Hata, T. Y., A. H. Hara, and B. K. S. Hu. 1997, Molluscicides and mechanical barriers against slugs, *Vaginula plebeian* Fischer and *Veronicella cubensis* (Pfeiffer) (Stylommatophora: Veronicellidae). Crop-prot. 16 (6): 501-506). It was also discovered that the borate prevented the bait from going moldy throughout the duration of this study and this is seen as an additional benefit of the invention. This evaluation determined that boric acid has molluscicidal properties and that the proposed composition is an effective attractant to snails and slugs. A snail and slug bait containing boric acid is also likely to be more effective and last longer than other snail and slug baits available due to its fungicidal properties.

Weather Testing Study

Weatherized granular bait made in accordance with the invention was tested in exposed exterior situations for a period of one month to determine its ability to withstand weathering conditions typical of the environment of snails and slugs. The active ingredient concentration in the bait was determined and plotted against the recorded amount of rainfall over the exposed period as well as exposure over time.

The granular bait used in this weathering test contained about 5% boric acid as the active ingredient and a combination of both lipid and carbohydrate attractants. The objective of this study was to determine the effectiveness of this process and the longevity of product performance by determining the rate of active ingredient loss due to exterior exposure. Three open stations, each containing 100-grams of the granular bait product and a perforated base were placed outside in 3 different open locations. A sample was taken from each station at regular intervals and the total rainfall was recorded using a rain gauge. This continued for about 1 month and until a total of >6 inches of rain had passed though the granular bait.

Following exposure, samples were oven dried at 35 degrees Celsius overnight. 5 grams of each sample was then taken and placed into 245 grams of water in a round bottom flask. This gave a dilution factor of 50. The flask was connected to a condenser and refluxed for 30 minutes to solubilize all available borate. The heat source was then removed and the flask allowed to cool with an inverted small beaker on the top of the condenser. Once cooled, the contents of the flasks were filtered using a Whatman 541 paper and the filtrate was analyzed for boric acid content using a standard mannitol titration. A suitable aliquot of the extract was taken and weighed (W). Dilute hydrochloric acid was added to lower the pH to 3 or 4, then 0.05M sodium hydroxide was added until a pH of 5.8 was reached, and burette reading noted. Excess mannitol (15 grams) was then added to the flask, and this was titrated back to 5.8 with 0.05M sodium hydroxide, again noting the burette reading. The concentration of borate as % boric acid equivalent (BAE) was then determined using the following calculation.

$$(\% \text{ BAE}=((\text{Titre}/W) \times N \times 6.1823) \times 50 \text{ (dilution factor)}.$$

where Titre (total volume of NaOH used)=R1-R2

Figure 4:
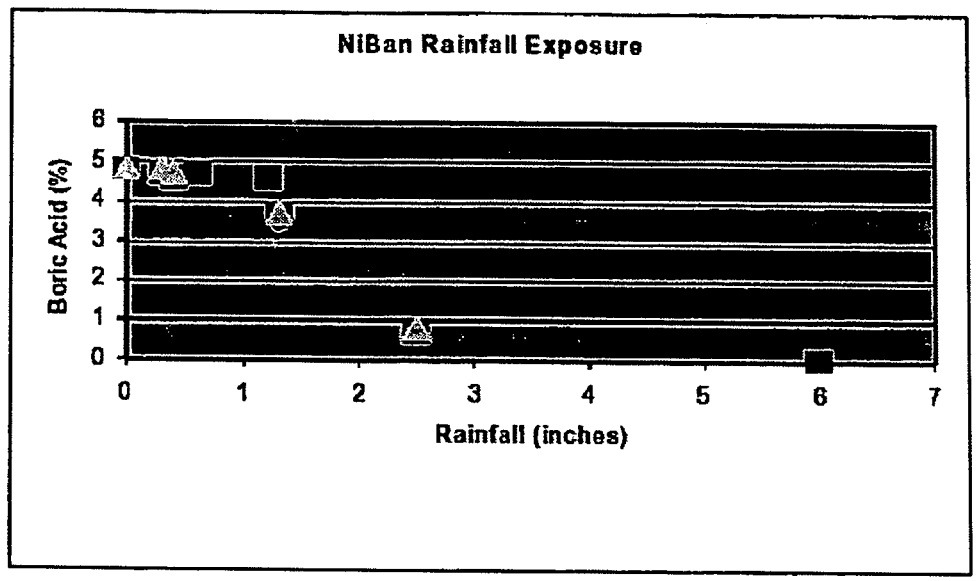
FIG. 4 is a chart showing the weather resistance of compositions made in accordance with the invention.
Figure 5:
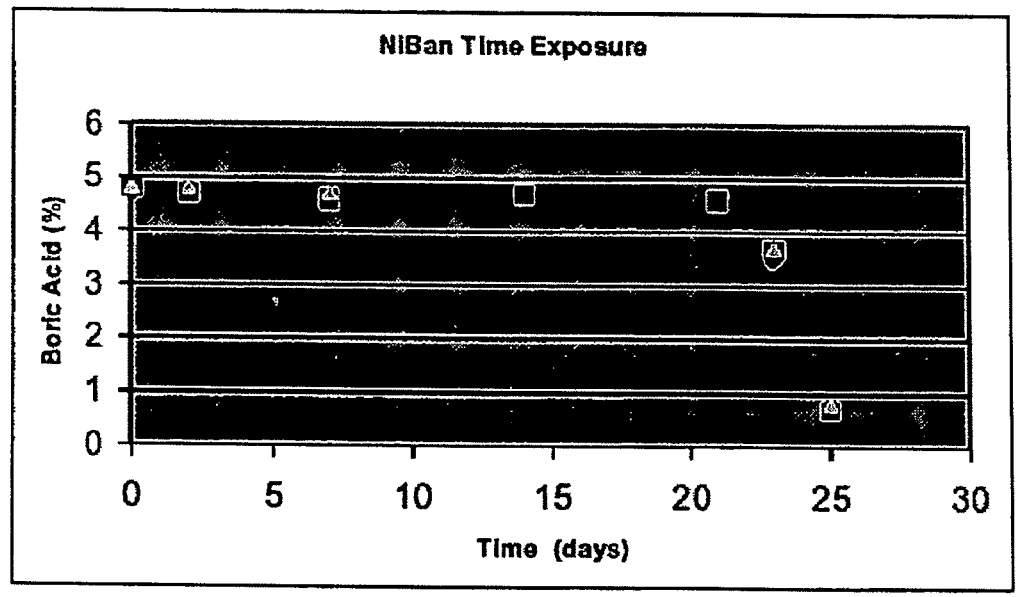
FIG. 5 is a second chart showing the weather resistance of compositions made in accordance with the invention.

The analytical results have been shown against rainfall in Table 1 and FIG. 4, and against time in Table 2 and FIG. 5.

TABLE 1

Active Ingredient Content Compared to Rainfall

| Sample | Rainfall (Inches) | % BAE |
|---|---|---|
| 1 | 0 | 4.7, 4.8, 4.8 |
| 2 | 0.3 | 4.8, 4.7, 4.8 |
| 3 | 0.4 | 4.7, 4.6, 4.7 |
| 4 | 0.6 | 4.7, 4.7 |
| 5 | 1.2 | 4.6, 4.6 |
| 6 | 1.3 | 3.5, 3.7, 3.7 |

TABLE 1-continued

Active Ingredient Content Compared to Rainfall

| Sample | Rainfall (Inches) | % BAE |
|---|---|---|
| 7 | 2.5 | 0.8, 0.7, 0.8 |
| 8 | 6 | 0.04, 0.04 |

TABLE 2

Active Ingredient Content compared to Time

| Time (days) | % BAE |
|---|---|
| 0 | 4.7, 4.8, 4.8 |
| 2 | 4.8, 4.7, 4.8 |
| 7 | 4.7, 4.6, 4.7 |
| 14 | 4.7, 4.7 |
| 21 | 4.6, 4.6 |
| 23 | 3.5, 3.7, 3.7 |
| 25 | 0.8, 0.7, 0.8 |
| 27 | 0.04, 0.04 |

From these results it can be observed that the boric acid in the granular bait is slowly lost with increasing amounts of rainfall. From referring to various efficacy studies with a variety of insects, boric acid is known to be effective below 0.5% retention. Light rainfall that does not soak right through the sample did not appear to significantly affect the boric acid content of the bait, and this is probably the case as the sample simply gets wet and then dries out again. However, a heavy downpour of at least 2 inches significantly reduces the boric acid content. This probably occurs as free running water passes through the bait, both solubilizing and removing the boric acid.

From the graph of the same retention data plotted against time rather than rainfall (FIG. 5), it can be seen that simple exposure to air and sunlight did not correlate with borate loss.

This study found that the active ingredient was slowly lost with increasing rainfall, and that most loss occurred with a heavy downpour in a short period of time. From the results gained it was concluded that the granular bait of the invention will retain efficacy and performance for an exposed period equating to up to 4 inches of rainfall. However, it is recommended that re-application of granular bait be carried out after any period of continuous 2 inches of rainfall, 4 inches of total rainfall, or 3 months, whichever occurred first.

It can be concluded from this work that performance of the granular bait would be maintained for an extended period of time in the absence of rainfall and for up to 4 inches of accumulated rainfall. It is therefore recommended that re-application of the granular bait be carried out after any period of continuous 2 inches of rainfall, 4 inches of total rainfall, or 3 months, whichever occurred first.

The foregoing description of preferred embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A pest control composition comprising:
    from about 1 to about 15 percent of a borate-containing active ingredient selected from the group consisting of boric acid, boric oxide, sodium tetraborate, disodium octaborate, sodium pentaborate, and combinations thereof;
    from about 52 to about 75 percent of a cellulosic carrier matrix material selected from the group consisting of ground corn cobs, straw, wood particles, rice hulls, and combinations thereof;
    from about 10 to about 20 percent of an oil-based attractant selected from the group consisting of corn oil, peanut oil, soybean oil, palm oil, sunflower oil, rapeseed oil, and combinations thereof;
    from about 1 to about 8 percent of a protein-based attractant selected from the group consisting of soy-derived protein, egg-derived protein, myco-derived protein, bacteria-derived protein, fish-derived protein, insect-derived protein, bovine-derived protein, porcine-derived protein, and combinations thereof;
    from about 5 to about 15 percent of a sugar-based attractant selected from the group consisting of sucrose, dextrose, glucose, fructose, honey, corn syrup, maple syrup, and combinations thereof; and
    from about 5 to about 15 percent of a flour-based attractant comprising wheat flour or corn flour, wherein all weight percentages are based upon dry weight of the pest control composition;
    wherein the pest control composition is formed into pellets having a width of from about 3 to about 5 millimeters and a length of from about 6 to about 10 millimeters;
    wherein the oil-based attractant, the protein-based attractant, the sugar-based attractant, and the flour-based attractant combine to attract terrestrial mollusks; and
    wherein the pest control composition retains efficacy for exterminating terrestrial mollusks under wet or moist environmental conditions.

2. The pest control composition of claim 1, wherein the borate-containing active ingredient comprises boric acid.

3. The pest control composition of claim 1, wherein the oil-based attractant comprises corn oil.

4. The pest control composition of claim 1, wherein the sugar-based attractant comprises sucrose.

5. The pest control composition of claim 1, wherein the protein-based attractant comprises egg-derived protein.

6. The pest control composition of claim 1, wherein the pest control composition comprises:
    about 5 percent of the borate-containing active ingredient;
    about 57 percent of ground corn cobs;
    about 15 percent of the oil-based attractant;
    about 3 percent of the protein-based attractant;
    about 10 percent of the sugar-based attractant; and
    about 10 percent of the flour-based attractant.

7. The pest control composition of claim 1, wherein the flour-based attractant comprises particles having a particle size distribution such that at least about 80 weight percent of the flour-attractant particles pass through a number 14 U.S. standard sieve mesh screen and no more than about 20 weight percent of the flour-attractant particles pass through a number 40 U.S. standard sieve mesh screen.

8. The pest control composition of claim 1, wherein the cellulosic carrier matrix material comprises ground corn cobs.

9. The pest control composition of claim 1, wherein the pest control composition maintains at least a 3% concentration of a boric acid equivalent when exposed to at least 1.5 inches of rainfall.

10. The pest control composition of claim 1, wherein the pest control composition maintains at least a 3% concentration of a boric acid equivalent when exposed to a wet or moist environment for a period of at least 23 days.

11. The pest control composition of claim 1, wherein the pest control composition maintains efficacy for exterminating mollusks under wet or moist environmental conditions for a period of from about 1 month to about 3 months.

12. A method of controlling terrestrial mollusks in a wet or moist environment, the method comprising the steps of:
    providing a pest control composition which is durable under wet or moist environmental conditions in which terrestrial mollusks live and which comprises:
        from about 1 to about 15 percent of a borate-containing active ingredient selected from the group consisting of boric acid, boric oxide, sodium tetraborate, disodium octaborate, sodium pentaborate, and combinations thereof;
        from about 52 to about 75 percent of a cellulosic carrier matrix material selected from the group consisting of ground corn cobs, straw, wood particles, rice hulls, and combinations thereof;
        from about 10 to about 20 percent of an oil-based attractant selected from the group consisting of corn oil, peanut oil, soybean oil, palm oil, sunflower oil, rapeseed oil, and combinations thereof;
        from about 1 to about 8 percent of a protein-based attractant selected from the group consisting of soy-derived protein, egg-derived protein, myco-derived protein, bacteria-derived protein, fish-derived protein, insect-derived protein, bovine-derived protein, porcine-derived protein, and combinations thereof;
        from about 5 to about 15 percent of a sugar-based attractant selected from the group consisting of sucrose, dextrose, glucose, fructose, honey, corn syrup, maple syrup, and combinations thereof; and
        from about 5 to about 15 percent of a flour-based attractant comprising wheat flour or corn flour, wherein all weight percentages are based upon dry weight of the pest control composition;
    forming the pest control composition into pellets having a width of from about 3 to about 5 millimeters and a length of from about 6 to about 10 millimeters;
    applying the pest control composition to a wet or moist environment which is infested with terrestrial mollusks; and
    attracting terrestrial mollusks with the pest control composition so that the terrestrial mollusks ingest a lethal amount of the pest control composition;
    wherein the oil-based attractant, the protein-based attractant, the sugar-based attractant, and the flour-based attractant combine to attract terrestrial mollusks.

13. A pest control composition comprising:
    from about 1 to about 15 percent of a borate-containing active ingredient selected from the group consisting of boric acid, boric oxide, sodium tetraborate, disodium octaborate, sodium pentaborate, and combinations thereof;
    from about 1 to about 10 percent of an oil-based attractant selected from the group consisting of corn oil, peanut oil, soybean oil, palm oil, sunflower oil, rapeseed oil, and combinations thereof;

from about 1 to about 8 percent of a protein-based attractant selected from the group consisting of soy-derived protein, egg-derived protein, myco-derived protein, bacteria-derived protein, fish-derived protein, insect-derived protein, bovine-derived protein, porcine-derived protein, and combinations thereof;

from about 5 to about 15 percent of a sugar-based attractant selected from the group consisting of sucrose, dextrose, glucose, fructose, honey, corn syrup, maple syrup, and combinations thereof; and from about 72 to about 82 percent of a flour-based attractant comprising wheat flour or corn flour, wherein all weight percentages are based upon dry weight of the pest control composition;

wherein the pest control composition is formed into pellets having a width of from about 3 to about 5 millimeters and a length of from about 6 to about 10 millimeters;

wherein the oil-based attractant, the protein-based attractant, the sugar-based attractant, and the flour-based attractant combine to attract terrestrial mollusks; and wherein the pest control composition retains efficacy for exterminating terrestrial mollusks in wet or moist environmental conditions.

14. The pest control composition of claim 13, wherein the borate-containing active ingredient comprises boric acid.

15. The pest control composition of claim 13, wherein the oil-based attractant comprises corn oil.

16. The pest control composition of claim 13, wherein the sugar-based attractant comprises sucrose.

17. The pest control composition of claim 13, wherein the protein-based attractant comprises egg-derived protein.

18. The pest control composition of claim 13, wherein the pest control composition comprises:
about 5 percent of the borate-containing active ingredient;
about 5 percent of the oil-based attractant;
about 3 percent of the protein-based attractant;
about 10 percent of the sugar-based attractant; and
about 77 percent of the flour-based attractant.

19. The pest control composition of claim 13, wherein the pest control composition maintains at least a 3% concentration of a boric acid equivalent when exposed to at least 1.5 inches of rainfall.

20. The pest control composition of claim 13, wherein the pest control composition maintains at least a 3% concentration of a boric acid equivalent when exposed to a wet or moist environment for a period of at least 23 days.

21. The pest control composition of claim 13, wherein the pest control composition maintains efficacy for exterminating mollusks under wet or moist environmental conditions for a period of from about 1 month to about 3 months.

22. A method of controlling terrestrial mollusks in a wet or moist environment, the method comprising the steps of:
providing a pest control composition which is durable under wet or moist environmental conditions in which terrestrial mollusks live and which comprises:
from about 1 to about 15 percent of a borate-containing active ingredient selected from the group consisting of boric acid, boric oxide, sodium tetraborate, disodium octaborate, sodium pentaborate, and combinations thereof;
from about 1 to about 10 percent of an oil-based attractant selected from the group consisting of corn oil, peanut oil, soybean oil, palm oil, sunflower oil, rapeseed oil, and combinations thereof;
from about 1 to about 8 percent of a protein-based attractant selected from the group consisting of soy-derived protein, egg-derived protein, myco-derived protein, bacteria-derived protein, fish-derived protein, insect-derived protein, bovine-derived protein, porcine-derived protein, and combinations thereof;
from about 5 to about 15 percent of a sugar-based attractant selected from the group consisting of sucrose, dextrose, glucose, fructose, honey, corn syrup, maple syrup, and combinations thereof; and
from about 72 to about 82 percent of a flour-based attractant comprising wheat flour or corn flour, wherein all weight percentages are based upon dry weight of the pest control composition;
forming the pest control composition into pellets having a width of from about 3 to about 5 millimeters and a length of from about 6 to about 10 millimeters;
applying the pest control composition to a wet or moist environment which is infested with terrestrial mollusks; and
attracting terrestrial mollusks with the pest control composition so that the terrestrial mollusks ingest a lethal amount of the pest control composition;
wherein the oil-based attractant, the protein-based attractant, the sugar-based attractant, and the flour-based attractant combine to attract terrestrial mollusks.

* * * * *